(12) United States Patent
Seyfang et al.

(10) Patent No.: US 10,571,582 B2
(45) Date of Patent: Feb. 25, 2020

(54) METHOD AND APPARATUS FOR THE QUANTITATIVE MASS DETERMINATION OF THE CONTENT OF CLOSED FOIL PACKAGES

(71) Applicant: Harro Hoefliger Verpackungsmaschinen GmbH, Allmersbach im Tal (DE)

(72) Inventors: Karlheinz Seyfang, Allmersbach im Tal (DE); Martin Lober, Allmersbach im Tal (DE); Joachim Fahrian, Allmersbach im Tal (DE); Jan Rimbach, Erfurt (DE)

(73) Assignee: Harro Hoefliger Verpackungsmaschinen GmbH, Allmersback im Tal (DE)

( * ) Notice: Subject to any disclaimer, the term of this patent is extended or adjusted under 35 U.S.C. 154(b) by 118 days.

(21) Appl. No.: 15/970,649

(22) Filed: May 3, 2018

(65) Prior Publication Data
US 2018/0321401 A1    Nov. 8, 2018

(30) Foreign Application Priority Data
May 3, 2017   (EP) .................................... 17000757

(51) Int. Cl.
*G01T 7/00*    (2006.01)
*G01N 23/04*   (2018.01)
(Continued)

(52) U.S. Cl.
CPC ................. *G01T 7/005* (2013.01); *A61J 1/00* (2013.01); *G01G 9/005* (2013.01); *G01N 23/04* (2013.01); *A61J 1/035* (2013.01)

(58) Field of Classification Search
CPC . A61J 1/00; A61J 1/035; G01G 9/005; G01N 23/04; G01T 7/005
See application file for complete search history.

(56) References Cited

U.S. PATENT DOCUMENTS

2016/0140413 A1*  5/2016  Maga ..................... G01N 23/10
                                                        382/195
2017/0211966 A1   7/2017  Monz et al.

FOREIGN PATENT DOCUMENTS

WO    2009012097 A1   1/2009
WO    2012013368 A1   2/2012

* cited by examiner

*Primary Examiner* — Mark R Gaworecki
(74) *Attorney, Agent, or Firm* — Walter Ottesen, P.A.

(57) ABSTRACT

In a calibration routine, a first set of X-ray recordings of at least one closed first reference package without content is produced, and a mass calibration signature is derived therefrom. A second set of X-ray recordings of at least one closed second reference package having a reference content is produced, and a reference signature is derived therefrom. From the reference signature and the mass calibration signature, a reference measurement value is derived via subtraction. The reference mass of the reference content is ascertained by weighing and assigned to the reference measurement value. In ongoing measurement operation, at least one set of measuring X-ray recordings of closed foil packages each having a content is produced and a measurement signature is derived therefrom. Herefrom, and from the mass calibration signature, measurement values for the individual closed foil packages are derived via subtraction, from which the masses of the contents are quantitatively determined.

12 Claims, 4 Drawing Sheets

(51) Int. Cl.
*A61J 1/00* (2006.01)
*G01G 9/00* (2006.01)
*A61J 1/03* (2006.01)

METHOD AND APPARATUS FOR THE QUANTITATIVE MASS DETERMINATION OF THE CONTENT OF CLOSED FOIL PACKAGES

CROSS REFERENCE TO RELATED APPLICATION

This application claims priority of European patent application no. 17 000 757.9, filed May 3, 2017, the entire content of which is incorporated herein by reference.

FIELD OF THE INVENTION

The invention relates to a method and to an apparatus for the quantitative mass determination of the content of closed foil packages, wherein the foil packages each have at least one metallic foil layer.

BACKGROUND OF THE INVENTION

In particular in the case of small filling amounts, for example pharmaceutical powders or the like, it is not only difficult to perform exact and reproducible dosing, but it is also difficult to quantitatively determine or check the dosed and filled masses.

The use of X-ray devices for in-process filling control is known in principle. However, the use is associated with a series of problems. An X-ray image chain is relatively unstable compared to optical industrial cameras. Fluctuations in terms of brightness, spectral distribution and imaging geometry are relatively pronounced. Automated interpretation of the X-ray results is therefore possible in the prior art only to a limited extent, which consequently entails two different scenarios. In a first scenario, non-metallic packages, which are highly transmissive for X-rays, are X-rayed. The resulting X-ray signature can have a sufficiently fine resolution for allowing the performance of a quantitative mass determination of the content. In a second scenario, packages having one or more metallic foil layers are X-rayed. Such packages, for example from aluminum foil, have a very pronounced absorption effect for the X-rays passing through them, which is significantly higher than the absorption effect of the generally non-metallic package content. The signature of the X-ray image is thus dominated by the metallic foil and is influenced only to a comparatively small degree by the package content. The X-ray result therefore at best permits qualitative statements, which means statements as to whether a filling is present or not. Due to the pronounced shielding effect of the metallic foil, it is practically impossible to make quantitative statements, that is, statements regarding the amount of the filling mass. In simple terms, it is possible to determine whether the metallic foil package contains a filling, but not whether the filling exhibits deviations from the desired target mass.

SUMMARY OF THE INVENTION

It is an object of the invention to provide a method for quantitative mass determination of the content of closed foil packages, which can also be used for packages having at least one metallic foil layer.

This object can, for example, be achieved by a method for quantitative mass determination of the content of closed foil packages, wherein the foil packages each have filling spaces having a base area and an edge region outside the base area and at least one metallic foil layer. The method includes the steps of:—x-raying, in a calibration routine, at least one closed first reference package without content using an X-ray source and producing a first set of initial X-ray recordings thereof;—deriving a mass calibration signature from the first set of initial X-ray recordings;—x-raying at least one closed second reference package with a reference content using the X-ray source and producing a second set of initial X-ray recordings thereof;—deriving an initial reference signature from the second set of initial X-ray recordings;—deriving a reference measurement value from the initial reference signature and the mass calibration signature by way of subtraction;—quantitatively ascertaining the mass of the reference content of the at least one second reference package as a reference mass by weighing and assigning the reference mass to the reference measurement value;—terminating the calibration routine, wherein an ongoing measurement operation follows;—x-raying, in the ongoing measurement operation, closed foil packages each with a content using the X-ray source and producing at least one set of measuring X-ray recordings thereof;—deriving a measurement signature from the at least one set of measuring X-ray recordings, wherein a first sum signal is ascertained within the base area, a second sum signal is ascertained in the edge region, and the measurement signature is ascertained by subtraction between the first and the second sum signals;—deriving measurement values for the individual closed foil packages from the measurement signature and the mass calibration signature by way of subtraction; and,—quantitatively determining the masses of the contents of the closed foil packages from the measurement values taking into consideration the assignment of the reference mass to the reference measurement value.

It is a further object of the invention to provide an apparatus that is suitable for quantitative mass determination of the content of closed foil packages, which can also be used for packages having at least one metallic foil layer.

This object can, for example, be achieved by an apparatus for the quantitative mass determination of the content of closed foil packages, wherein the foil packages each have filling spaces having a base area and an edge region outside the base area and at least one metallic foil layer. The apparatus includes: an X-ray station having an X-ray source and an X-ray imaging device and having a control unit; the control unit being configured to:—x-ray, in a calibration routine, at least one closed first reference package without content using the X-ray source and produce a first set of initial X-ray recordings thereof;—derive a mass calibration signature from the first set of initial X-ray recordings;—x-ray at least one closed second reference package with a reference content using the X-ray source and produce a second set of initial X-ray recordings thereof;—derive an initial reference signature from the second set of initial X-ray recordings;—derive a reference measurement value from the initial reference signature and the mass calibration signature by way of subtraction;—quantitatively ascertain the mass of the reference content of the at least one second reference package as a reference mass by weighing and assigning the reference mass to the reference measurement value;—terminate the calibration routine, wherein an ongoing measurement operation follows;—x-ray, in the ongoing measurement operation, closed foil packages each with a content using the X-ray source and produce at least one set of measuring X-ray recordings thereof;—derive a measurement signature from the at least one set of measuring X-ray recordings, wherein a first sum signal is ascertained within the base area, a second sum signal is ascertained in the edge region, and the measurement signature is ascertained by subtraction between the first and the second sum signals;—derive measurement values for the individual closed foil packages from the measurement signature and the mass calibration signature by way of subtraction; and,—quantitatively determine the masses of the contents of the closed foil packages from the measurement values taking into consideration the assignment of the reference mass to the reference measurement value.

A calibration routine is performed before the ongoing measurement operation. In the calibration routine, at least one closed first reference package, preferably an entire set thereof, without content is produced and X-rayed using an X-ray source. A first set of initial X-ray recordings is made hereof using an X-ray imaging device. From this first set of initial X-ray recordings, a mass calibration signature is derived.

Furthermore, at least one closed second reference package, preferably an entire set thereof but this time each having a reference content, is produced and X-rayed using the X-ray source. A second set of initial X-ray recordings hereof is now produced, and an initial reference signature is derived therefrom. From this initial reference signature and from the mass calibration signature which was mentioned further above, a reference measurement value is derived through subtraction.

As part of the calibration routine, the mass of the content of the at least one second reference package is furthermore quantitatively ascertained as a reference mass by weighing and assigned to the previously mentioned reference measurement value. Next, the calibration routine is terminated, and the ongoing measurement operation follows.

During the ongoing measurement operation, the closed foil packages to be checked together with their content are X-rayed using the X-ray source. At least one set of X-ray recordings is made hereof as well, and a measurement signature is derived therefrom. From the measurement signature and from the mass calibration signature which was previously ascertained in the calibration routine, measurement values for the individual closed foil packages are derived by subtraction. Taking into consideration the assignment, likewise performed in the calibration routine, of the reference mass to the reference measurement value, it is now possible to not only qualitatively, but also quantitatively determine the masses of the contents of the closed foil packages from the measurement values of the ongoing measurement operation.

The invention proceeds from the finding that a reliable quantitative statement relating to the mass of the package content can be made if the influence of the foil package is taken into consideration in a specific manner and is eliminated to a sufficient degree. One essential problem that has been found is that the forming process of the metallic foil is subject to locally distributed tolerances. In a row or matrix of molds and associated stamps, the metallic foil is plastically formed into blister cavities or the like, which, due to dimensional tolerances, leads to slightly different flow behavior of the foil in the region of each individual mold. This in turn results in individually significant X-ray signatures in the associated individual packages. The individual deviations, however, are reproducible. In other words, each set of foil packages originating from a row or matrix of molds has a comparable distribution of the individually significant X-ray signatures. The distribution is then ascertained during the calibration routine using the above-mentioned mass calibration signature. In the subsequent ongoing measurement operation, in the case of the filled foil packages to be checked, a comparable distribution of the signature which is individually significant for the package material will form. As a consequence, the then performed subtraction has the result that the signature distributions that are produced solely by the package material but are equally present in both signatures cancel one another. In sum, their influence disappears or is reduced to a manageable degree. Instead, after the subtraction a signature remains that can be assigned completely, or at least predominantly, to the package content as measurement value. By way of the assignment of the reference mass to the reference measurement value, which is also performed as part of the calibration routine, it is now possible to derive from the ongoing measurement values very precise quantitative mass information relating to the individual package fillings.

In summary, it is thus possible with a method according to the invention and an apparatus according to the invention to achieve reliable elimination of the locally varying disturbing influence of the metallic foil using subtraction with the result that, despite dominant shielding by the metallic foil, a quantitative mass determination is obtained.

The term "set" of X-ray recordings, which is variously used here, includes at least one individual recording. However, such a set preferably includes multiple recordings of the respectively same state, which are overlaid by calculation means, or superposed, to form an overall recording. It is possible in this way to reduce image noise and other disadvantageous effects.

It may suffice to apply a method according to the invention or an apparatus according to the invention to individual packages. However, it is preferred to produce a set of measuring X-ray recordings of a plurality of foil packages together, arranged in particular in the form of a matrix, in the ongoing measurement operation. In correspondence therewith, first and second sets of initial X-ray recordings of reference packages with and without reference contents, but in the same number and in the same spatial arrangement as the foil packages, are produced first in the previous calibration routine. This is where the full benefits are reaped: Even though, within such a group or row or matrix of foil packages, the X-ray signature generated by the formed foil varies and is individual for each row or matrix position, the differences between these signatures, which are individually different yet recurring in their distribution, can be eliminated by the above-described subtraction, with the result that, despite the individually different packages, it is possible to derive measurement values that for their part allow unique deductions to be drawn as to the degree of filling of the individual packages within the entire set thereof.

In an advantageous embodiment, a calibration of the image chain using a previously taken set of X-ray recordings, which are produced without interposition of reference packages or foils, is performed at the start of the calibration routine. Hereby, various properties of the X-ray recording are taken into consideration. Unlike in typical optical image recordings, imaging in the case of X-ray recordings is effected via central projection, in which the X-rays proceed from a nearly point-shaped radiation source and are projected onto the X-ray imaging device. The radiation intensity that is incident on the flat X-ray imaging device is dependent on the square of the distance from the radiation source. Due to the central projection, this square of the distance is greater in the edge regions of the X-ray imaging device than in the central region, with the result that an uneven brightness distribution with darker edge regions and a lighter central region is obtained. Gray level distribution and gray level conversion are not homogeneous over the area of the X-ray imaging device and additionally are subject to age-related drift. These negative influences, however, can be largely suppressed by the above-mentioned calibration of the image chain, that is, on the basis of reference recordings of homogeneous areas without foil or blister or package influence.

The individual foil packages have filling spaces with a base area. In an advantageous embodiment, a first sum signal is ascertained within this base area. In addition, a second sum signal is ascertained outside the base area, but, directly adjacent thereto, in the edge region of the foil package. The different signatures including the measurement signature which was already mentioned further above are then ascertained by subtraction between the first and second sum signals. Hereby, further disturbing influences can be ruled out, which results in a further improvement of the measurement result for mass determination. This is because it has been observed that the central, nearly point-shaped X-ray source varies in brightness and position. This causes constant changes in brightness, spectral distribution and imaging geometry. The X-ray image chain is thus temporally relatively unstable, at least compared to an optical industrial camera having LED illumination. In addition, the foils used vary in terms of the material thickness, which is even more pronounced due to variations in the sealing process. In other words, temporally varying influences of the package material are produced in addition to the variations in the imaging. However, it is assumed within the context of the invention that the variations, although present, have a uniform effect within small spatial extents. Since the first and the second sum signal are ascertained within the base area of an individual filling space and in the immediately adjacent edge region, the above-mentioned temporal variations substantially have the same effect for both sum signals. The subtraction between the two sum signals which then follows consequently eliminates the variation influences, with the result that the measurement values for the mass determination of the package content are freed from them. The previously described approach is equally applicable for the determination of the mass calibration signature, the reference signature and the measurement signature.

A further improvement can be attained by the first and second sum signals being linearized. This simplifies in particular the transformation of the measurement signature into a measurement value for the mass of the package content. This is because there is a linear relationship between the mass to be ascertained and the value of the measurement signature. For a corresponding linear regression function, the determination of two points thus suffices. A first point, specifically an offset point, was already ascertained in the first, empty reference packages. The second point is obtained from the initial reference signature or from the reference measurement value after the second reference package, which is provided with a filling whose mass is known, has been X-rayed. The first-mentioned value consequently corresponds to a filling mass equaling zero, while the second value mentioned corresponds to a specific mass ascertained by weighing. Due to the established linear relationship, it is possible by way of linear interpolation or by linear extrapolation to simply and exactly derive the associated filling mass from each desired measurement value in the ongoing measurement operation.

Another problem to be considered is that the foil webs during processing by the forming station are drawn through the subsequent filling station and the likewise subsequent sealing station all the way to the X-ray checking station. This has the result that the orientation of the individual package filling spaces is not always exactly known. For this reason, initial image signatures are derived which are characteristic of the shape and position of the base areas of individual foil packages. These serve as a reference for what is known as "pattern matching," as a result of which position determinations or position corrections are then performed during the ascertaining of the first and second sum signals. It is possible to ensure hereby that the first sum signals can be assigned uniquely to the filling spaces and the second sum signals can be assigned uniquely to the surrounding edge regions.

BRIEF DESCRIPTION OF THE DRAWINGS

The invention will now be described with reference to the drawings wherein.

DESCRIPTION OF THE PREFERRED EMBODIMENTS OF THE INVENTION

Figure 2:
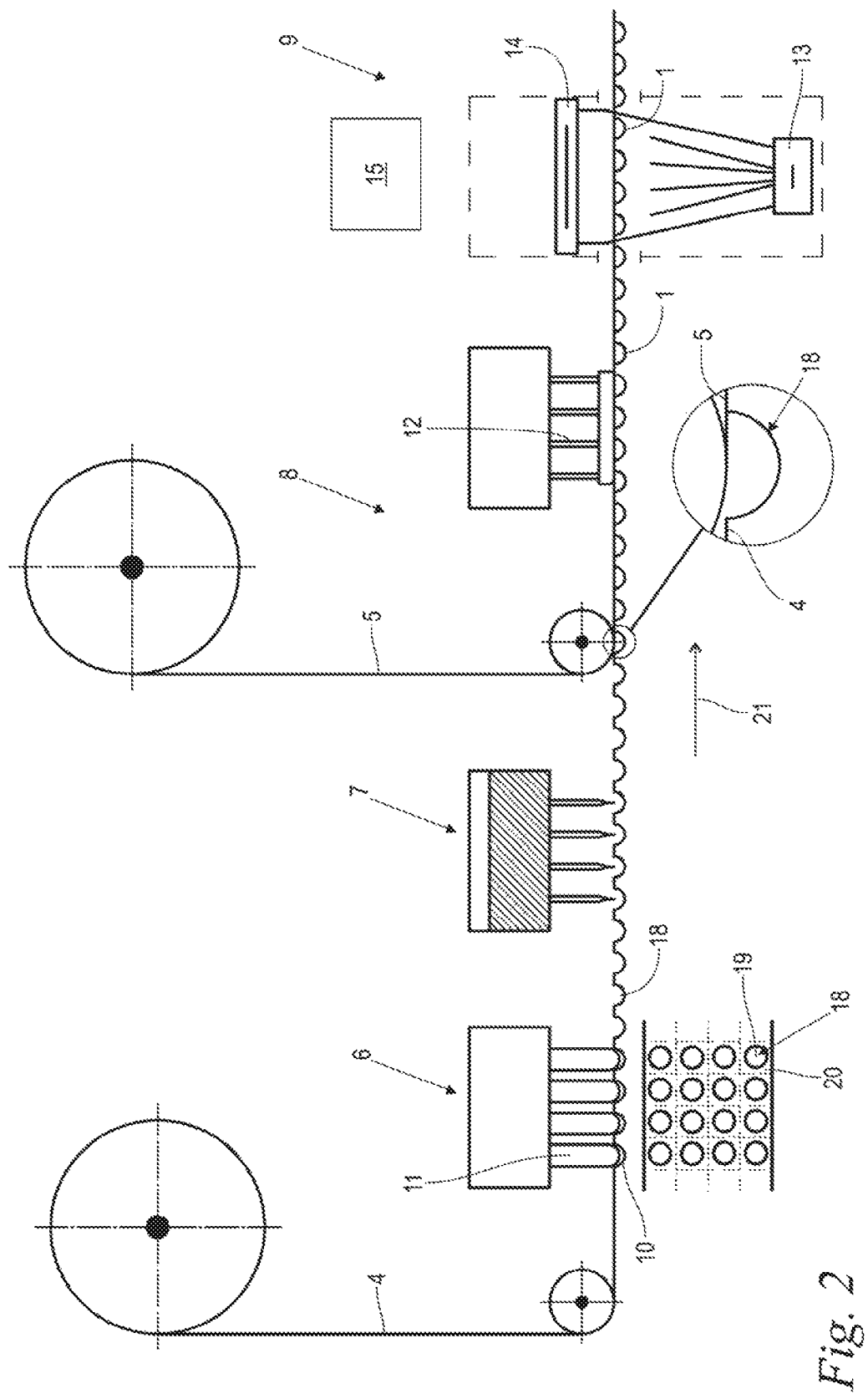
FIG. 2 shows the arrangement according to FIG. 1 in the calibration routine during the ascertainment of a mass calibration signature on empty reference packages.
Figure 3:
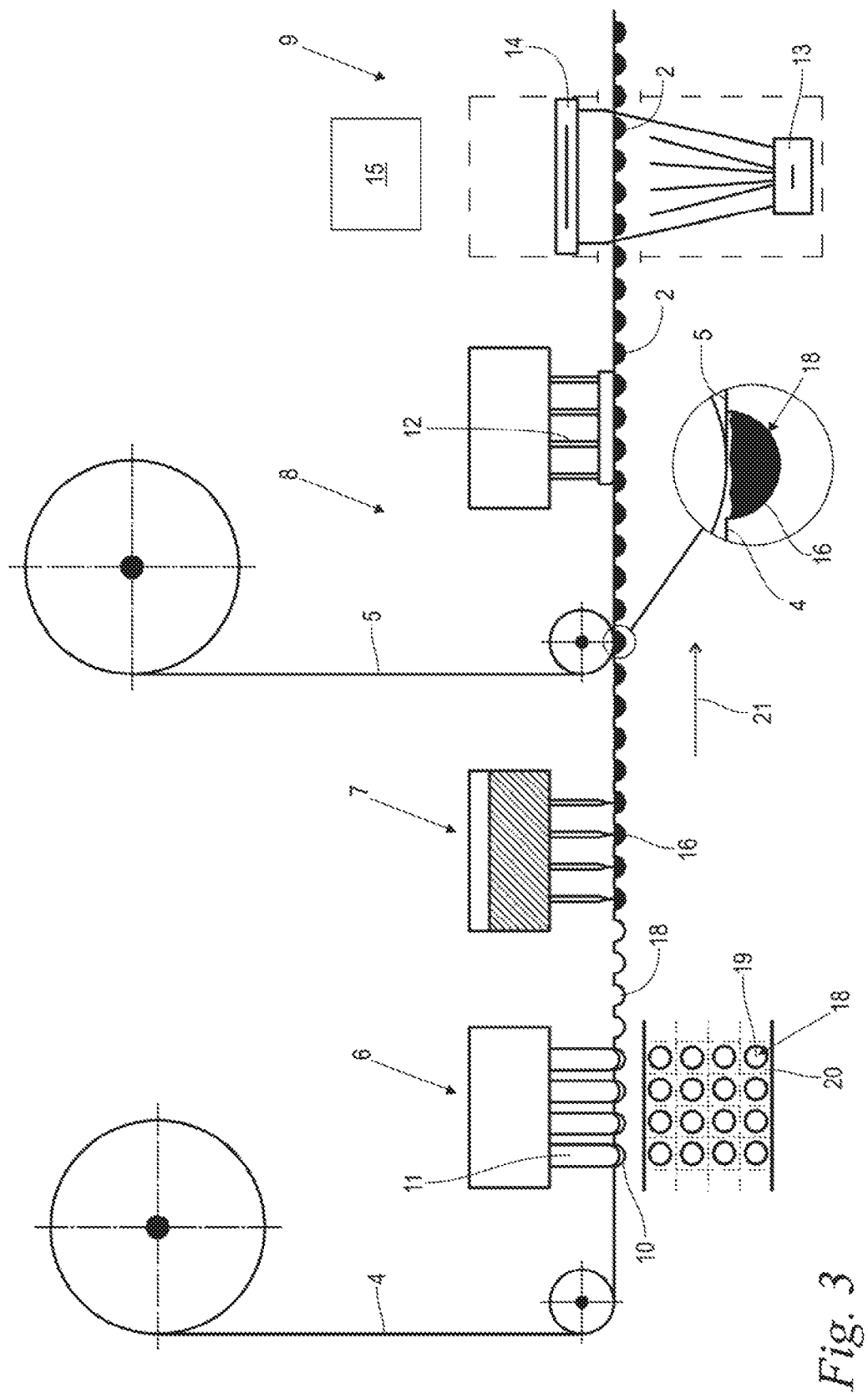
FIG. 3 shows the arrangement according to FIG. 1 and FIG. 2 in the calibration routine during the ascertainment of an initial reference signature on filled reference packages; and, FIG. 4 shows the arrangement according to FIGS. 1 to 3 in the ongoing production and measurement operation during a mass determination of the package contents using the X-ray station calibrated in accordance with FIGS. 1 to 3.
Figure 4:
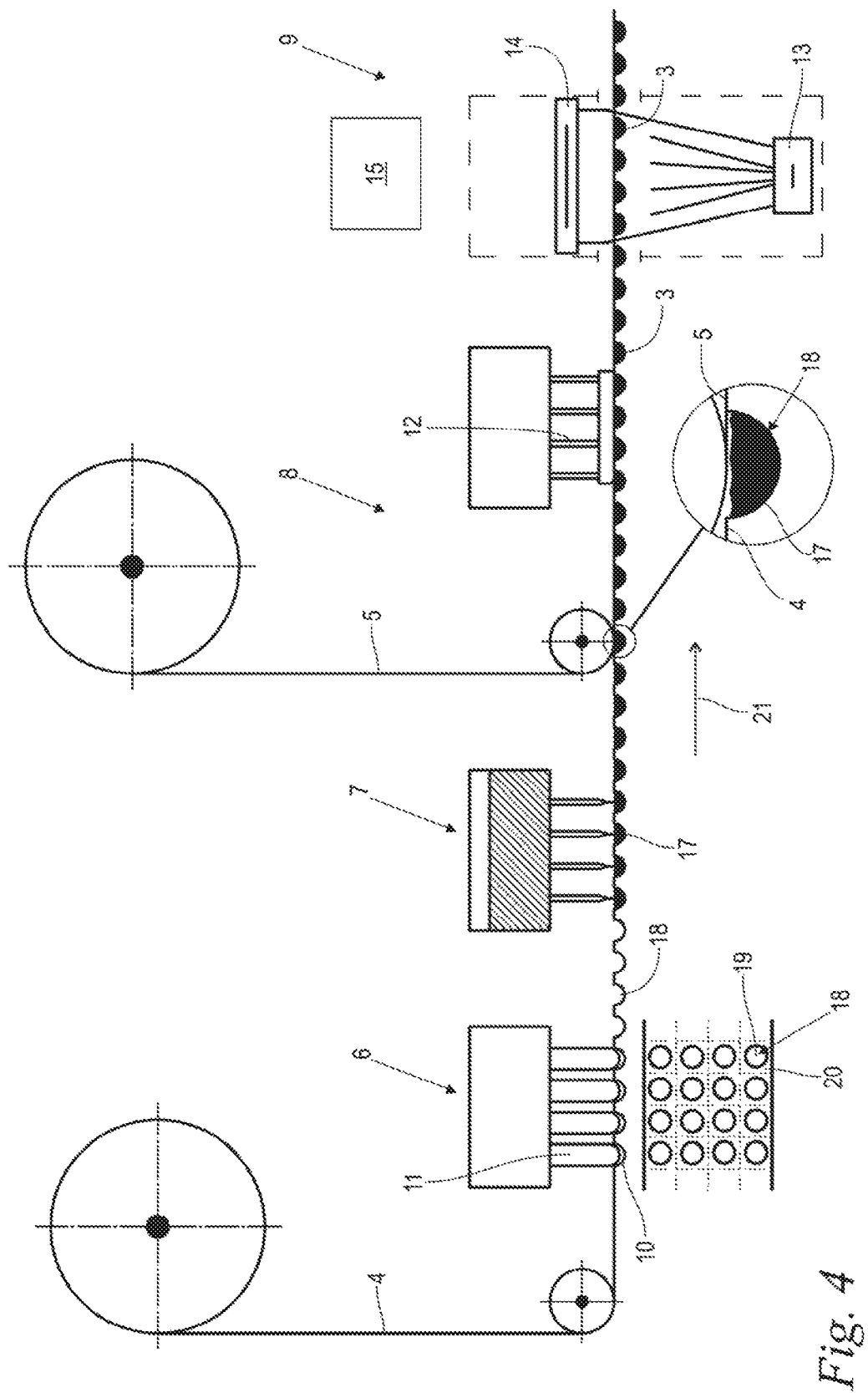

FIGS. 1 to 4 show a schematic block illustration of a forming and filling facility for foil packages 3 which are described in connection with FIG. 4.

The foil packages 3 each have at least one, in the present case even two, metallic foil layers (4, 5) and are additionally each filled with a content 17 (FIG. 4). The latter can be, for example, pharmaceutical powder. However, different contents 17 can also be taken into consideration. The arrangement shown here not only serves for the production of the filled foil packages 3, but in particular also for a 100% in-process control by way of quantitative mass determination of the individual contents 17 of all foil packages 3 by way of a destruction-free test, which can be performed using the invention despite the problematic influence of the at least one metallic foil layer 4, 5.

The facility includes a forming station 6, a filling station 7, and a sealing station 8, the functions of which will be described further below in connection with FIGS. 2 and 3. Following these, an X-ray station 9, having an X-ray source 13 and an X-ray imaging device 14, are situated at the output side of the sealing station 8. Located in the X-ray source 13 is an at least approximately point-shaped radiation source, whose graphically indicated rays are incident, in the form of a central projection, on the X-ray imaging device 14, which is formed as a flat panel. The X-ray imaging device 14 is in the form of a pixel matrix, which produces finely resolved gray level images in dependence on the intensity of the incident X-rays using a downstream, schematically indicated control unit 15. The X-ray station 9 and in particular the control unit 15 are configured as an apparatus for performing a method according to the invention which is described below.

Figure 1:
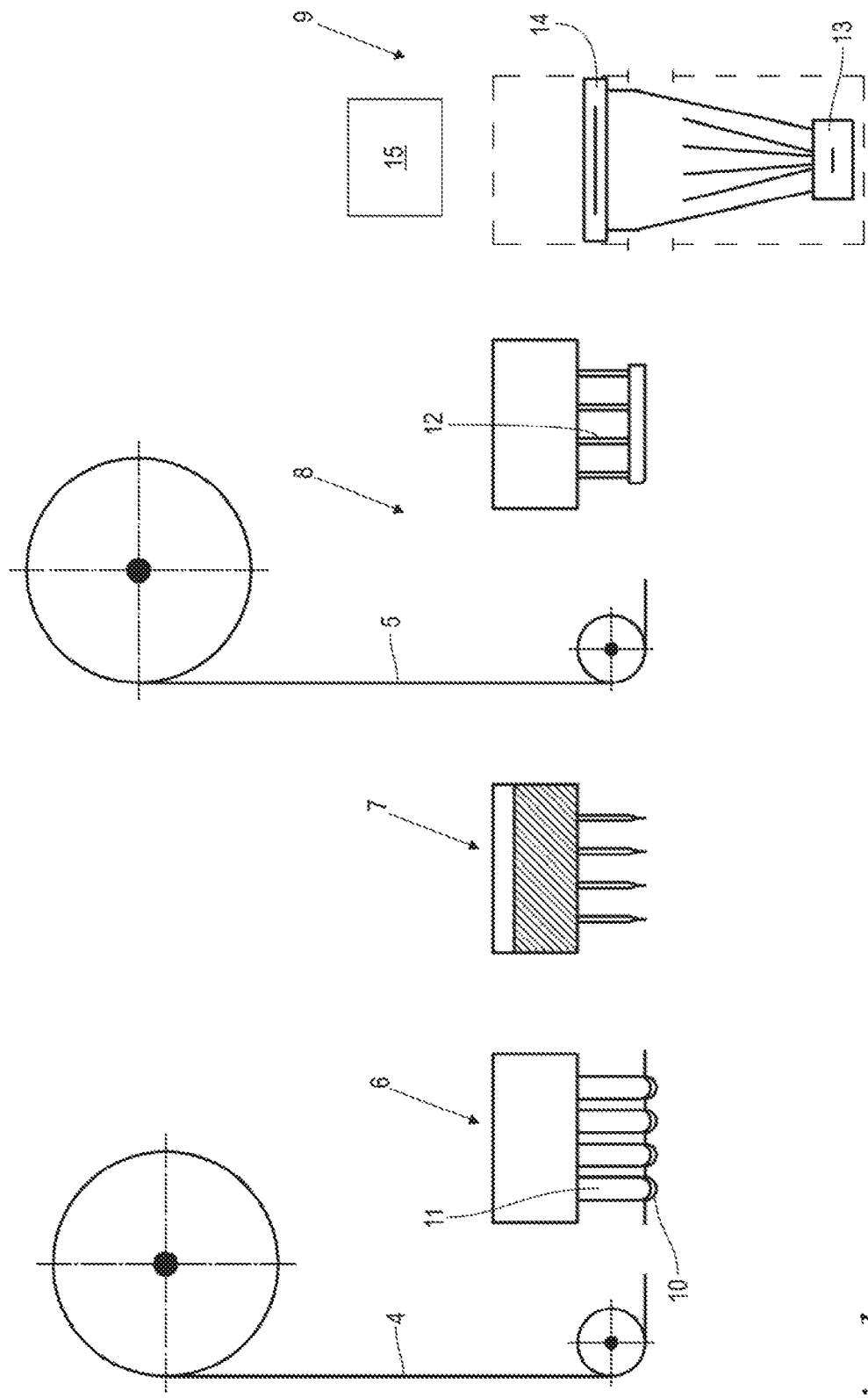
FIG. 1 shows a schematic block illustration of a forming and filling facility for foil packages having an integrated X-ray station according to the invention during an initial calibration of the image chain.

Before the start of an ongoing production and measurement operation, which will be described further below in connection with FIG. 4, first a calibration routine is performed. A first step of the calibration routine is illustrated in FIG. 1. Here, the forming, filling and sealing stations 6, 7, 8 are initially not yet in operation and without function. No package material is located between the X-ray source 13 and the X-ray imaging device 14 in the X-ray station 9. The image chain, including the X-ray source 13 and the X-ray imaging device 14, is now calibrated. To this end, a first, prior set of X-ray recordings is produced using the X-ray source 13 and the X-ray imaging device 14. Since no package material or the like is positioned between the X-ray source 13 and the X-ray imaging device 14, superposed images of a homogeneous area are recorded in this way. Hereby, a latently present non-uniform brightness distribution on the area of the X-ray imaging device 14 is ascertained. The distribution serves for a now performed gray level calibration routine, such that at each individual pixel of the X-ray imaging device 14 equally calibrated gray levels can be assumed.

FIG. 2 shows the arrangement according to FIG. 1 in the next step of the calibration routine. Here, first at least one, in the preferred embodiment shown a plurality of, first reference packages 1 arranged in the form of a matrix are produced. The first reference packages 1 are empty, that is, contain no content at all. They are made from the same material and in the same configuration as the second reference packages 2 (FIG. 3), which will be described below, and the foil packages 3 (FIG. 4), which are produced in the later ongoing operation. They each include at least one metallic foil layer 4, 5. In the embodiment shown, they are formed by a bottom metallic foil layer 4 and an upper metallic foil layer 5. The term metallic foil layer in this connection means that metal, such as aluminum or the like, is used distributed over an area such that it is relevant for a later X-raying process for the imaging. That is, they can be pure metal foils. It is of course also possible for metal foils having paper or plastic lamination to be used, which also includes coatings with sealing adhesive or the like. In the embodiment shown, the two foil layers 4, 5 are metallic foil layers. It is, however, likewise feasible for only one of them to be in the form of a metallic foil layer. In any case, what is said here does not only apply to the embodiment of the first reference packages 1, which are described here in connection with FIG. 2, but also to the second reference packages, which will be described later in connection with FIGS. 3 and 4, and also to the foil packages 3, which are produced in the later ongoing operation.

First, the bottom foil layer 4 is drawn from a roller and supplied to the forming station 6. The latter includes a number of forming molds 10 having associated forming stamps 11. This number may be a single forming mold 10 and a single associated forming stamp 11. Preferably, a plurality of forming molds 10 and associated forming stamps 11 are used, which are arranged for example in a row or, as shown here, in the form of a matrix. Using a stroke motion, the stamps 11 plunge into the forming molds 10 with interposition of the bottom foil layer 4. The bottom metallic foil layer 4 thus undergoes cold forming such that a matrix-shaped group or a set of filling spaces 18 is simultaneously impressed into the bottom foil layer 4. Shown schematically below the forming station 6 in plan view is the bottom foil layer 4, according to which the filling spaces 18 are arranged in the matrix shape and in each case have a base area 19 which is circular here only by way of example. Any other suitable desired shape of a base area 19 can of course be selected. In any case, the individual filling spaces 18 with their base areas 19 are surrounded in each case by a directly adjacent edge region 20.

The bottom foil layer 4, which is thus provided with impressed filling spaces 18, is now guided in a feed direction indicated by an arrow 21 to the sealing station 8. In the process, it passes the filling station 7, which is positioned therebetween but remains without function in this method step. The filling spaces 18 are not filled. The upper foil layer 5 is drawn from a roll at the sealing station 8 and placed onto the bottom foil layer 4 such that it covers the filling spaces 18 which initially remain open toward the top. Sealing stamps 12 of the sealing station 8 now seal the upper foil layer 5 onto the edge regions 20 of the bottom foil layer 4 in a known hot-sealing method, such that a set of first reference packages 1 without content is produced.

Such a set of closed first reference packages 1, the individual reference packages 1 of which are positioned in the form of a matrix as schematically indicated at the forming station 6, is now advanced in the feed direction 21 to the X-ray station 9 and positioned between the X-ray source 13 and the X-ray imaging device 14. Once this set of first reference packages 1 has arrived and stopped, it is X-rayed using the X-ray source 13 such that a first set of initial X-ray recordings is produced on the X-ray imaging device 14. A mass calibration signature, which is distributed over the area of the X-ray imaging device 14 or over the area of the set of first reference packages 1, is derived therefrom in the control unit 15. The mass calibration signature corresponds to the gray level distribution as is produced by a set of empty packages without any content influencing the gray level distribution.

Subsequently, the next method step is performed as part of the calibration routine, as is illustrated in FIG. 3. To this end, first a set of closed, second reference packages 2 is produced. This production uses the same foil layers 4, 5 with the same production method as in FIG. 2 in likewise the same number and spatial arrangement, that is, the same matrix form. The only difference is that now, the filling station 7 is used after the forming process in the forming station 6, but before the sealing station 8 is reached. The filling station 7 is used to fill a reference content 6 into all filling spaces 18 of the set of second reference packages 2. The reference content 16 is in particular the same material as used in the case of the content 17 of the foil packages 3 which is filled in later in the ongoing production operation (FIG. 4). At any rate, once sealing has been completed at the sealing station 8, a set of closed second reference packages 2 is obtained, wherein, in contrast to the first reference packages 1 according to FIG. 2, the individual reference packages 2 are not empty but contain a reference content 16.

This set of closed second reference packages 2 is now guided in the feed direction 21 to the X-ray station 9, where it comes to be between the X-ray source 13 and the X-ray imaging device 14 and is stopped. As was the case for the first reference packages 1, the set of second reference packages 2 is now X-rayed using the X-ray source 13, wherein a second set of initial X-ray recordings is produced using the X-ray imaging device 14. From the second set, once again a signature is derived in the control unit 15, in this case an initial reference signature. In contrast to the above-described mass calibration signature, the initial reference signature corresponds to the gray level distribution that is produced by the sum of the package material and the respective reference contents 16.

It has been found in connection with the invention that the forming molds 10, the forming stamps 11 and the local forming of the bottom foil layer 4 that is effected thereby are subject to tolerance-related deviations to such an extent that it is relevant for the formation of a measurement value. The same in terms of meaning also applies, for example, to locally varying influences during sealing in the sealing station 8. Such local deviations or spatial distributions can also be found within a set of packages as static signature differences in comparison with the individual reference packages 1, 2 or foil packages 3. In addition, the static signature differences are reproducible during the production of the first reference packages 1, the production of the second reference packages 2 and the production of the regular foil packages 3, described further below, within a set of packages or within a matrix thereof, that is, they re-occur in each production step. For this reason, this results in a subtraction between the initial reference signature with filling influence, described here, and the mass calibration signature without filling influence, described above in connection with FIG. 2. As a result of the subtraction, the static signature differences of the reference signature and the mass calibration signature, which remained the same, cancel each other out, as a result of which the influence of the foil layers 4, 5 is eliminated. The subtraction only leaves reference measurement values that can be assigned to the individual reference contents 16. In addition, the individual masses of the individual reference contents 16 are quantitatively ascertained as a respective reference mass by weighing and assigned to the previously mentioned reference measurement values. In other words, for each row, matrix or other arrangement of the packages which are handled at the same time, groups of tuples of filling mass and reference measurement values (reference gray level sums) are formed and group-specific regression functions are calculated therefrom.

Performed next is a linearization described further below, such that a linear relationship between reference measurement value and reference mass can be produced. The calibration routine is now terminated.

Once the calibration routine is terminated, the ongoing production and measurement operation is performed. Here, foil packages 3 with individual contents 17 are produced and subjected in the X-ray station 9 according to FIG. 3 to a 100% in-process control with quantitative mass determination. The production of the foil packages 3 with the respective contents 17 is performed analogously to the production of the second reference packages 2 with the reference contents 16, which also includes the number and distribution of the filling spaces 18 with their base areas 19 and edge regions 20 within a simultaneously produced set of foil packages 3 or of second reference packages 2. Even the material of the foil layers 4, 5 is the same. For this reason, reference is made at this point to the equally applicable description relating to FIG. 3. The only difference is that, for the calibration routine, in each case one set of first reference packages 1 and second reference packages 2 suffices, while in ongoing operation according to FIG. 4, any desired number of sets of foil packages 3 is produced in successive cycles and checked.

In ongoing operation, a contiguous set of foil packages 3 is guided, analogously to the illustration according to FIG. 3, to the X-ray station 9 and positioned here between the X-ray source 13 and the X-ray imaging device 14. Here, the contiguous line of foil packages 3 is stopped. In each case one identification number is assigned to the individual foil packages 3.

Analogously to the method step in accordance with FIG. 3, the closed foil packages 3 with a respective content 17 are now X-rayed using the X-ray source 13, such that a set of measuring X-ray recordings is produced on the X-ray imaging device 14. A measurement signature is derived therefrom in the control unit 15. The measurement signature manifests as a gray level distribution which corresponds to the individual foil packages 3 and their contents 17. To save time, the calculation steps required herefor and also the steps which are yet to be described are preferably performed once the control unit 15 has already initiated the next processing cycle, within which the next set of filled foil packages 3 are supplied to the X-ray station 9. It may of course also be expedient to leave the just X-rayed set of foil packages 3 in the X-ray station 9 until the evaluation of the mass determination is complete.

Analogously to the final method step of the calibration routine in accordance with FIG. 3, a subtraction is also performed in the ongoing measurement operation in accordance with FIG. 4, but this time between the just produced measurement signature with influence of the contents 17 and the mass calibration signature without influence of any contents in accordance with FIG. 2. Here, analogously to the illustration in accordance with FIG. 3, static signature differences or signature distributions between the individual filling spaces 18 are also eliminated. The subtraction leaves only measurement values that can be assigned to the individual contents 17 of the individual foil packages 3 and to the associated identification numbers. Since, in addition, in the calibration step in accordance with FIG. 3, an assignment of reference mass to reference measurement value was performed and corresponding regression functions were ascertained, it is possible on that basis to perform a quantitative determination of the masses of the individual contents 17 from the current measurement values with a high degree of accuracy.

The above-described method steps take into consideration the static, recurring signature differences between the different reference packages 1, 2 or foil packages 3 within an individual set thereof, but not temporal variations that occur due to brightness variations in the image chain of the X-ray station 9 or thickness variations in the foil layers 4, 5. However, these temporal variations can be eliminated by way of the mass calibration signature in accordance with FIG. 2, the reference signature in accordance with FIG. 3 and the measurement signature in accordance with FIG. 4 being ascertained analogously as follows: FIGS. 2, 3 and 4 and the schematic block illustration in the region of the respective forming station 6 show that the individual reference packages 1, 2 and foil packages 3 each have filling spaces 18 having a base area 19, and that the base areas 19 are surrounded, immediately adjacently thereto, by edge regions 20. In all three cases, first, a first sum signal is ascertained, which represents the gray level sum or the integral of the gray levels over the respective base area 19. In addition, a second sum signal is ascertained, which covers the directly adjacent edge region 20 and represents the local gray level sum or the integral of the gray levels over the edge region 20. By way of subtraction between the respective first and second sum signals, the mass calibration signature in accordance with FIG. 2, the reference signature in accordance with FIG. 3 and the measurement signature in accordance with FIG. 4 are ascertained. Since the above-mentioned temporal brightness variations have, at least in the region of an individual reference package 1, 2 or an individual foil package 3, equal effect on the associated first sum signal and the associated second sum signal, these effects are completely eliminated due to the subtraction.

This naturally assumes that it is possible to differentiate exactly between the base area 19 of the filling space 18 and the surrounding edge region 20. For this reason, first image signatures are derived from measurements of reference packages 1, 2 or foil packages 3, which image signatures are characteristic of the position of the base areas 19 of the filling spaces 18. By what is known as "pattern matching" it is now possible, using the characteristic, ideal-typical image signatures, as it were, to perform by way of calculation position determinations or position corrections for the base area 19, such that the first and the second sum signals can be ascertained in an exactly defined manner and separated from one another.

In addition, linearization of the first and second sum signals has proven useful. There is a linear relationship between the gray levels or measurement values ascertained in accordance with FIG. 4 for the individual filling spaces 18 and the masses of the respectively contained contents 17.

At any rate, in the context of a 100% in-process control for each individual content 17 of the filling spaces 18 of all foil packages 3, an exact quantitative mass determination is performed despite the presence of at least one metallic foil layer 4, 5. The respective numerical mass or weight values are then assigned to the individual identification numbers of the individual foil packages 3. For each individual foil package 3, it is then possible to make a statement as to what mass its content has, and/or whether in each case a content 17 with the desired mass, within a specified tolerance, is present or not.

It is understood that the foregoing description is that of the preferred embodiments of the invention and that various changes and modifications may be made thereto without departing from the spirit and scope of the invention as defined in the appended claims.

What is claimed is:

1. A method for quantitative mass determination of the content of closed foil packages, wherein the foil packages each have filling spaces having a base area and an edge region outside the base area and at least one metallic foil layer, the method comprising the steps of:
    x-raying, in a calibration routine, at least one closed first reference package without content using an X-ray source and producing a first set of initial X-ray recordings thereof;
    deriving a mass calibration signature from the first set of initial X-ray recordings;
    x-raying at least one closed second reference package with a reference content using the X-ray source and producing a second set of initial X-ray recordings thereof;
    deriving an initial reference signature from the second set of initial X-ray recordings;
    deriving a reference measurement value from the initial reference signature and the mass calibration signature by way of subtraction;
    quantitatively ascertaining the mass of the reference content of the at least one second reference package as a reference mass by weighing and assigning the reference mass to the reference measurement value;
    terminating the calibration routine, wherein an ongoing measurement operation follows;
    x-raying, in the ongoing measurement operation, closed foil packages each with a content using the X-ray source and producing at least one set of measuring X-ray recordings thereof;
    deriving a measurement signature from the at least one set of measuring X-ray recordings, wherein a first sum signal is ascertained within the base area, a second sum signal is ascertained in the edge region, and the measurement signature is ascertained by subtraction between the first and the second sum signals;
    deriving measurement values for the individual closed foil packages from the measurement signature and the mass calibration signature by way of subtraction; and,
    quantitatively determining the masses of the contents of the closed foil packages from the measurement values taking into consideration the assignment of the reference mass to the reference measurement value.

2. The method of claim 1, wherein a set of measuring X-ray recordings of a plurality of foil packages together is produced in the ongoing measurement operation; and, in the preceding calibration routine, first and second sets of initial X-ray recordings of reference packages with and without reference content, in the same number and the same spatial arrangement, are produced.

3. The method of claim 2, wherein the plurality of foil packages are arranged in the form of a matrix.

4. The method of claim 1 further comprising performing, at the beginning of the calibration routine, a calibration of an image chain using a prior set of X-ray recordings without reference packages.

5. The method of claim 1 further comprising linearizing the first sum signal and the second sum signal.

6. The method of claim 1 further comprising:
    deriving image signatures which are characteristic of the position of the base areas of the filling spaces from the set of measuring X-ray recordings; and,
    performing position corrections for the ascertainment of the first sum signal and the second sum signal.

7. An apparatus for the quantitative mass determination of the content of closed foil packages, wherein the foil packages each have filling spaces having a base area and an edge region outside the base area and at least one metallic foil layer, the apparatus comprising:
    an X-ray station having an X-ray source and an X-ray imaging device and having a control unit;
    said control unit being configured to:
    x-ray, in a calibration routine, at least one closed first reference package without content using said X-ray source and produce a first set of initial X-ray recordings thereof;
    derive a mass calibration signature from the first set of initial X-ray recordings;
    x-ray at least one closed second reference package with a reference content using said X-ray source and produce a second set of initial X-ray recordings thereof;
    derive an initial reference signature from the second set of initial X-ray recordings;
    derive a reference measurement value from the initial reference signature and the mass calibration signature by way of subtraction;
    quantitatively ascertain the mass of the reference content of the at least one second reference package as a reference mass by weighing and assigning the reference mass to the reference measurement value;
    terminate the calibration routine, wherein an ongoing measurement operation follows;
    x-ray, in the ongoing measurement operation, closed foil packages each with a content using said X-ray source and produce at least one set of measuring X-ray recordings thereof;
    derive a measurement signature from the at least one set of measuring X-ray recordings, wherein a first sum signal is ascertained within the base area, a second sum signal is ascertained in the edge region, and the measurement signature is ascertained by subtraction between the first and the second sum signals;

derive measurement values for the individual closed foil packages from the measurement signature and the mass calibration signature by way of subtraction; and, quantitatively determine the masses of the contents of the closed foil packages from the measurement values taking into consideration the assignment of the reference mass to the reference measurement value.

8. The apparatus of claim 7, wherein said control unit is configured to produce a set of measuring X-ray recordings of a plurality of foil packages together in the ongoing measurement operation, and, in the preceding calibration routine, produce first and second sets of initial X-ray recordings of reference packages with and without reference content, in the same number and the same spatial arrangement.

9. The apparatus of claim 8, wherein the plurality of foil packages are arranged in the form of a matrix.

10. The apparatus of claim 7, wherein said control unit is further configured to perform, at the beginning of the calibration routine, a calibration of an image chain using a prior set of X-ray recordings without reference packages.

11. The apparatus of claim 7, wherein said control unit is further configured to linearize the first sum signal and the second sum signal.

12. The apparatus of claim 7, wherein said control unit is further configured to:

derive image signatures which are characteristic of the position of the base areas of the filling spaces from the set of measuring X-ray recordings; and, perform position corrections for the ascertainment of the first sum signal and the second sum signal.

* * * * *